United States Patent
Braun et al.

(10) Patent No.: US 9,030,663 B2
(45) Date of Patent: May 12, 2015

(54) REMOTE ABSORPTION SPECTROSCOPY BY CODED TRANSMISSION

(75) Inventors: Michael G. Braun, Fort Wayne, IN (US); Jeremy T. Dobler, Fort Wayne, IN (US)

(73) Assignee: Exelis Inc., McLean, VA (US)

( * ) Notice: Subject to any disclaimer, the term of this patent is extended or adjusted under 35 U.S.C. 154(b) by 805 days.

(21) Appl. No.: 13/285,292

(22) Filed: Oct. 31, 2011

(65) Prior Publication Data

US 2013/0107263 A1    May 2, 2013

(51) Int. Cl.

| | |
|---|---|
| *G01N 21/00* | (2006.01) |
| *G01J 3/433* | (2006.01) |
| *G01N 21/3504* | (2014.01) |
| *G01J 3/02* | (2006.01) |
| *G01N 21/31* | (2006.01) |
| *G01J 1/42* | (2006.01) |

(52) U.S. Cl.
CPC .............. *G01J 3/433* (2013.01); *G01N 21/3504* (2013.01); *G01J 3/0297* (2013.01); *G01J 2001/4242* (2013.01); *G01N 21/314* (2013.01); *G01N 2021/3513* (2013.01)

(58) Field of Classification Search
CPC .............. G01J 3/42; G01J 3/10; G01J 3/0224; G01J 3/0264; G01J 3/0272; G01J 3/0283; G01J 3/108; G01J 3/2803; G01J 3/2823; G01J 3/44; G01J 3/4406; G01J 3/443; G01J 1/02; G01J 2001/4242; G01J 3/02
See application file for complete search history.

(56) References Cited

U.S. PATENT DOCUMENTS

| | | | |
|---|---|---|---|
| 4,425,503 | A | 1/1984 | Watkins et al. |
| 4,594,511 | A | 6/1986 | Cooper et al. |
| 6,949,734 | B2 | 9/2005 | Neff et al. |
| 7,009,170 | B2 | 3/2006 | Dobbs et al. |
| 7,102,751 | B2 | 9/2006 | Harper |
| 7,361,922 | B2 | 4/2008 | Kameyama et al. |
| 8,552,391 | B2 * | 10/2013 | Terenetska et al. ...... 250/370.07 |
| 2011/0150035 | A1 * | 6/2011 | Hanson et al. ................ 374/161 |

FOREIGN PATENT DOCUMENTS

| | | |
|---|---|---|
| EP | 2096421 A1 | 9/2009 |
| WO | 2010038058 A1 | 4/2010 |

OTHER PUBLICATIONS

T. Kraetschmer et al., "Background-free absorption spectroscopy using delayed balanced detection," Applied Physics B; Lasers and Optics, Copyright Spring-Verlag 2009, Berlin, Germany, vol. 98, No. 2-3, Dec. 11, 2009, XP019779927.
Extended European Search Report in counterpart Application No. 12186822.8, mailed Jan. 28, 2013.

* cited by examiner

*Primary Examiner* — Michael P Stafira
(74) *Attorney, Agent, or Firm* — Edell, Shapiro & Finnan LLC

(57) ABSTRACT

Remote absorption spectroscopy uses coded electromagnetic transmission directed through a medium under investigation to one or more remote receivers. The coded transmission includes at least one wavelength coincident with an absorption band of interest and one wavelength in an off-line band and a predefined relationship between spectral components in and outside the absorption band is controlled. The relationship between spectral components may be evaluated at the receiver to determine whether deviation thereof from the controlled relationship at the transmitter exists at the receiver. The deviation of the received optical signal from the prescribed relationship is processed to indicate the absorption of the radiation in the absorption band.

21 Claims, 9 Drawing Sheets

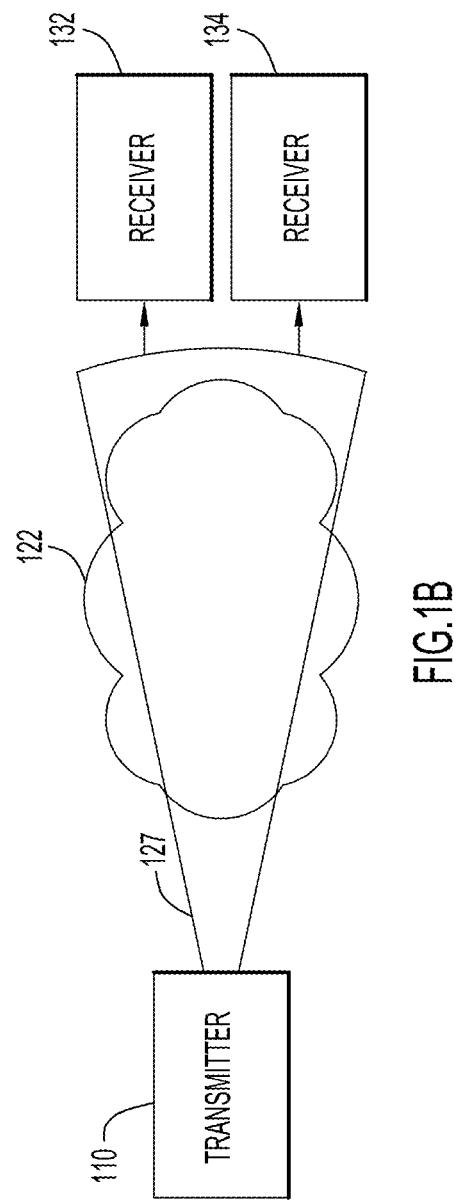

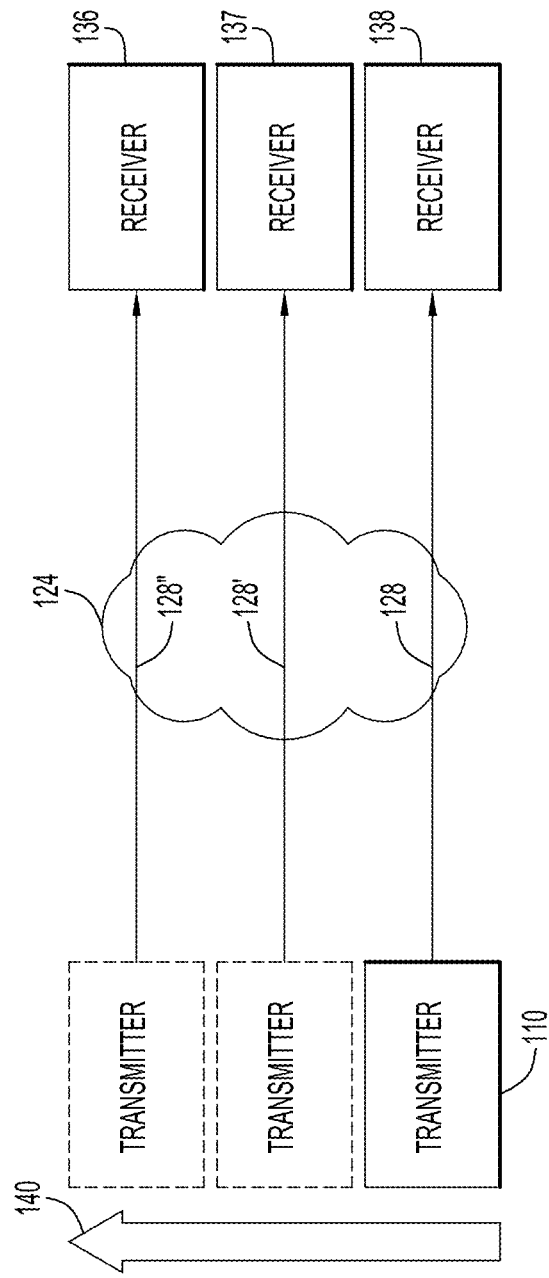

REMOTE ABSORPTION SPECTROSCOPY BY CODED TRANSMISSION

BACKGROUND

Conventional active source absorption spectroscopy systems for analyzing gases, such as $CO_2$, $CH_4$, $O_2$, etc. implement collocated transmitter and receiver components and, as such, require a short path length or reflections to return transmitted signals to the source location. Over long distances, the transmitted signals are reflected off mirrors or the ground to effect the return of the signal to the collocated receiver. Scattered returns from aerosol constituents or particles in these systems give rise to an additive error from backscattered radiation. This error effectively reduces the measured absorption, since the backscattered return completes only a partial path through the medium being analyzed. Additionally, if the reflector used is diffuse, large range-squared losses in the system result, prohibiting long-range implementation of the overall system.

In light of the shortcomings of these and other techniques, the need has been felt for a technique to measure constituents in a medium or the atmosphere so that partial path scattered return is ignored and to reduce transmission power losses where only diffuse targets exist for reflecting transmitted radiation.

SUMMARY

Described herein is a technique applicable to remote absorption spectroscopy using spatially isolated and arbitrarily located transmitter and receiver subsystems. Multispectral electromagnetic radiation may be generated to have spectral content coinciding with both an absorption band of a medium and an off-line band. The radiation may be modified prior to transmission, such as by a set of codes, to define a relationship between at least one spectral component in the absorption band and at least one spectral component in the off-line band. This relationship is controlled to be temporally constant and is known at the receiver. The receiver accepts the transmitted radiation through line-of-sight propagation through the medium and the spectral content of the received radiation is analyzed. Deviation of the spectral content of the received radiation from the relationship defined by the transmitter may be attributable to absorption by the medium of the spectral component inside the absorption.

The above and still further features and advantages of the present inventive concept will become apparent upon consideration of the following definitions, descriptions and descriptive figures of specific embodiments thereof. While these descriptions go into specific details of certain embodiments of the inventive concept, it is to be understood that variations may and do exist and will be apparent to those skilled in the art upon review of this disclosure.

BRIEF DESCRIPTION OF THE DRAWINGS

FIGS. 1A-1C illustrate various system configurations for remote absorption spectroscopy embodying the present general inventive concept;

DETAILED DESCRIPTION

Figure 1A:
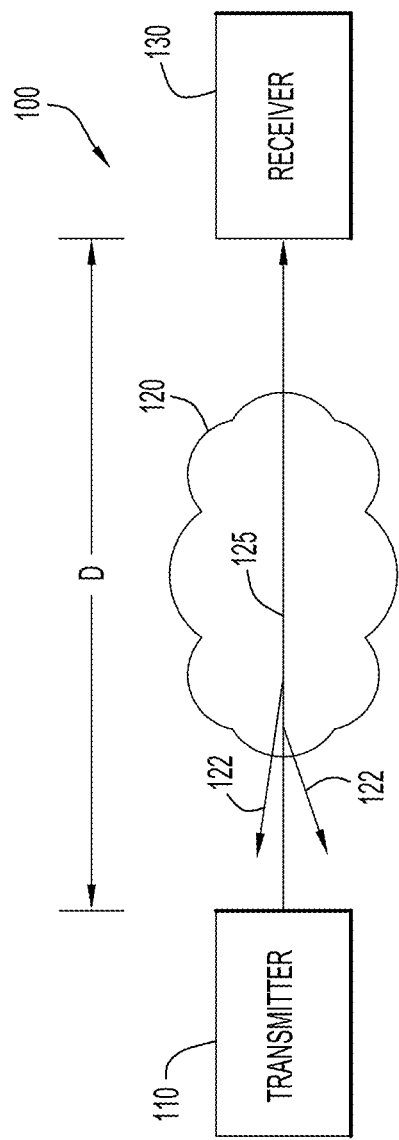

The present inventive concept is best described through certain embodiments thereof, which are described in detail herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light.

Additionally, mathematical expressions may be contained herein and those principles conveyed thereby are to be taken as being thoroughly described therewith. It is to be understood that where mathematics are used, such is for succinct description of the underlying principles being explained and, unless otherwise expressed, no other purpose is implied or should be inferred. It will be clear from this disclosure overall how the mathematics herein pertain to the present invention and, where embodiment of the principles underlying the mathematical expressions is intended, the ordinarily skilled artisan will recognize numerous techniques to carry out physical manifestations of the principles being mathematically expressed.

In FIG. 1A, there is illustrated an exemplary remote absorption spectrometer (RAS) 100 by which the present invention can be embodied. A transmitter 110 and a receiver 130 are separated by a distance D and the volume between transmitter 110 and receiver 130 is occupied by a medium 120 to be analyzed. Toward that end, transmitter 110 transmits a multispectral electromagnetic beam 125 through medium 120 to receiver 130, which accepts and analyzes electromagnetic beam 125 as transformed by properties of medium 120. At least one spectral band of beam 125 is selected to correspond to an absorption band of the constituent of medium 120 that is to be measured. Other spectral bands of beam 125 may be selected to coincide with other absorption bands, and still others may be used as reference signals.

Transmitter 110 may define and control a relationship between certain spectral components of beam 125, and provide knowledge of such relationship to receiver 130. As used herein, the term spectral component refers to a constituent spectral element of electromagnetic radiation and the term spectral content refers to the spectral makeup of the radiation over a predetermined range thereof. Thus, spectral components are distributed over the spectrum of the radiation to comprise the spectral content thereof. Receiver 130 may analyze the received spectral components of beam 125 and resolve absorption properties of medium 120 from the knowledge of the transmitted spectrum. Receiver 130 may make certain corrections to compensate for the system configuration and path-dependent variables caused by such configuration.

RAS 100 may be deployed in medium 120 that is substantially unbounded, such as the atmosphere and, as illustrated in FIG. 1A, 125 may be transmitted from transmitter 110 to receiver 130 through line-of-sight propagation. As used herein, the term line-of-sight propagation refers to propagation of electromagnetic radiation in a direction from transmitter 110 to receiver 130 so as to exclude detection and processing of electromagnetic radiation propagating towards transmitter 110, such as by scattering 122 illustrated in FIG. 1A. Under this definition, line-of-sight propagation does not exclude the use of reflectors as long as such reflection is excluded from traversing the transmitted beam.

Transmitter 110 and receiver 130 may be arbitrarily locatable such that the path length D through medium 120 can be varied on a deployment basis. Distance D between transmitter 110 and receiver 130 may be limited by system configuration, e.g., transmitter power and receiver sensitivity, but the present invention may be embodied for distances ranging from a few meters to hundreds of kilometers, as will be appreciated by the ordinarily skilled artisan upon review of this disclosure.

In FIG. 1B, an alternative embodiment allows transmitter 110 to transmit a beam 127 through a medium 122, where such beam is of sufficient width to be received simultaneously through line-of-sight propagation at multiple receivers 132, 134. Electromagnetic beam 127 may be spectrally similar to that described with reference to FIG. 1A, but with a broader beamwidth established through suitable beamforming techniques at transmitter 110. In yet a further implementation illustrated in FIG. 1C, transmitter 110 may be transported through a trajectory 140, such as by aircraft or by satellite, and an electromagnetic beam, representatively illustrated as beam 128, 128' and 128", may be received through line-of-sight propagation through medium 124 at distributed receivers 136-138 as transmitter 110 moves along trajectory 140. When multiple receivers are used, such as in the configurations of FIG. 1B and FIG. 1C, the absorption analysis performed at each receiver may be aggregated in a manner that provides an absorption profile of an extended region in space.

Figure 2:
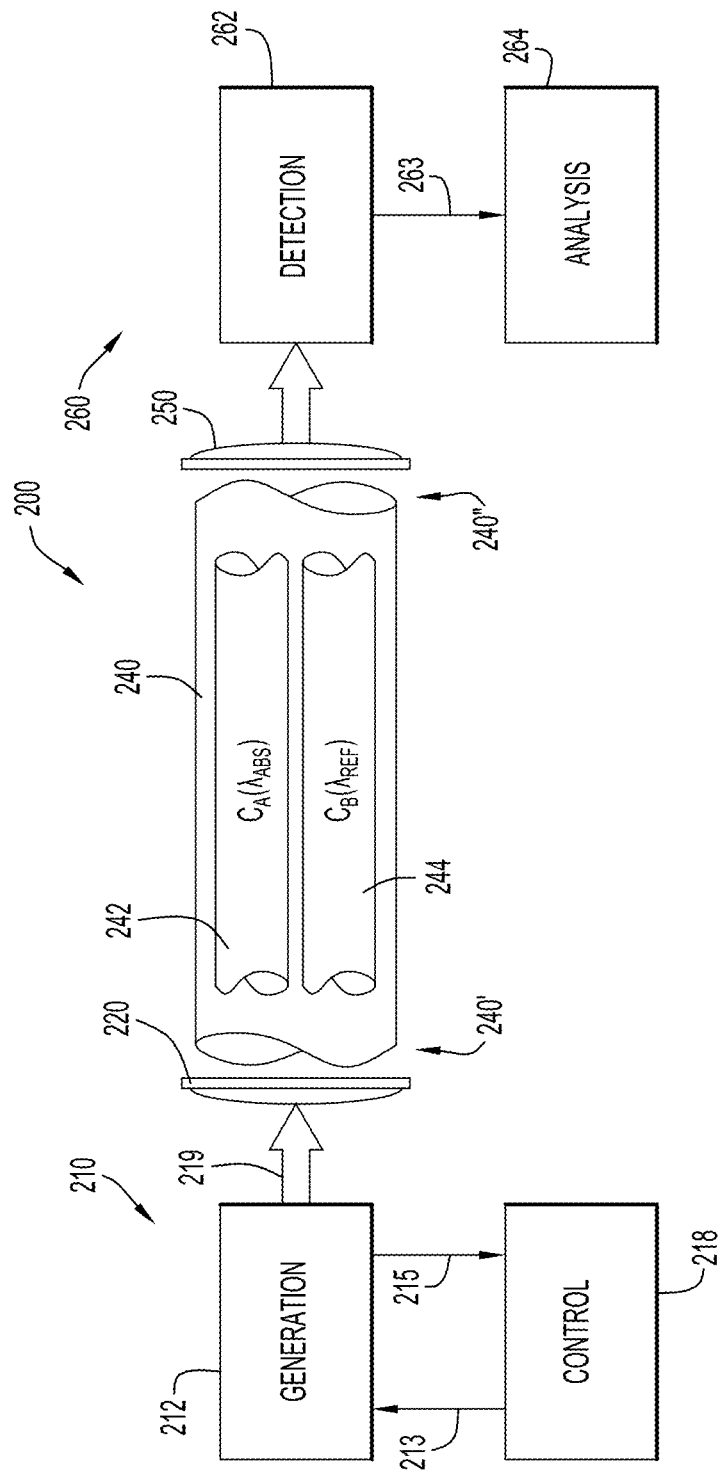
FIG. 2 is a high level diagram of an exemplary remote absorption spectrometer (RAS) embodying the present general inventive concept.

In the exemplary embodiment illustrated in FIG. 2, RAS 200 comprises a transmitter 210 to transmit an electromagnetic beam 240, indicated as transmitted beam 240', and a receiver 260 to receive beam 240, indicated as received beam 240", and to determine therefrom absorption characteristics of a medium through which beam 240 passes. Exemplary transmitter 210 is implemented through radiation generator 212, which may include radiation sources, such as, for example, lasers, diodes, magnetrons, vacuum tubes, etc., and radiation processing systems, such as, for example, focusing optics, modulators, filters, level monitors, etc. Transmitter 210 may include further a beamforming system 220, through which transmitted beam 240' is formed and delivered to the medium under study. Beamforming system 220 may include beamforming components suitable to the operating electromagnetic band of the RAS 200, including, but not limited to refractive elements, such as lenses, reflective elements, such as mirrors, radiators, such as antennas, frequency-selective elements, such as filters, and other elements by which beam 240 can be transmitted in a desired beam pattern.

Exemplary transmitter 210 includes a controller 218, through which the spectral content of transmitted beam 240' is established and controlled. Beam 240 includes, for example, spectral components $C_A(\lambda_{ABS})$, referred to herein as components 242, and spectral components $C_B(\lambda_{REF})$, referred to herein as components 244, where $C_A(\bullet)$ and $C_B(\bullet)$ are modulation coding functions on electromagnetic radiation having wavelengths $\lambda_{ABS}$ and $\lambda_{REF}$, respectively. It is to be understood that the notation $C_X(\lambda_X)$ carries with it the implication of an electromagnetic spectrum containing spectral components $\lambda_X$ generated by radiation sources, such as lasers, and spectral components generated by the application of coding function $C_X(\bullet)$ on $\lambda_X$, such as through modulation.

Wavelength $\lambda_{ABS}$ may be chosen to coincide with an absorption band of a chemical constituent of the medium under study and $\lambda_{REF}$ may be chosen to lie in an off-line band for purposes of reference. As used herein, an off-line band is a band in the electromagnetic spectrum of beam 240 that excludes $\lambda_{ABS}$. In certain embodiments, $\lambda_{REF}$ is chosen to lie in a spectral region where absorption is less than that at $\lambda_{ABS}$.

Coding functions $C_A(\bullet)$ and $C_B(\bullet)$ may be chosen to differentiate spectral components 242, 244 at receiver 260 and may be chosen to take on temporally-variable states, such as in amplitude, phase, etc., so that spectral properties of beam 240 can be controlled per a prescribed criterion. For example, $C_A(\bullet)$ and $C_B(\bullet)$ may be independent amplitude modulation functions of different modulation frequencies that can identify respective components 242, 244. The amplitudes of the modulation functions can be independently varied to control spectral energy in each of the transmitted components 242, 244, denoted herein as $P(\lambda_{ABS})$ and $P(\lambda_{REF})$. For example, the modulation amplitudes may be controlled so that $P(\lambda_{ABS})$ and $P(\lambda_{REF})$ are relatively maintained in accordance with a prescribed relationship, which may be, for example, proportionality. At receiver 260, under the assumption that the relationship between $P(\lambda_{ABS})$ and $P(\lambda_{REF})$ is constant at transmitter 210, variations in that relationship at receiver 260 can be attributed with confidence to absorption by the medium. The ordinarily skilled artisan may recognize other coding schemes that may be used in conjunction with the present invention without departing from the spirit and intended scope thereof. The scope of the present invention is intended to embrace such alternative schemes.

The application of $C_A(\bullet)$ and $C_B(\bullet)$ on $\lambda_{ABS}$ and $\lambda_{REF}$ may redistribute the energy of the spectral content of beam 240. Such redistribution may be over a very large spectral range. For example, to measure absorption of $CO_2$, $\lambda_{ABS}$ may be 1.5711194 microns and $\lambda_{REF}$ may be 1.57116194 microns. $C_A(\bullet)$ may be sinusoidal amplitude modulation at, say, 50 kHz and $C_B(\bullet)$ may be sinusoidal amplitude modulation at, say, 53 kHz. When $C_A(\bullet)$ is applied to $\lambda_{ABS}$, some of the energy originally at 1.5711194 microns is redistributed to 6.0 km. Similarly, the application of $C_B(\bullet)$ to $\lambda_{REF}$ redistributes some of the energy originally at 1.57116194 microns to 5.7 km. Receiver 260 may be configured to reject radiation outside, say, the micron range and, as such, would certainly not detect changes in energy levels in the kilometer range. However, changes in energy levels in the band containing 1.5711194-1.57116194 microns may be detectable at receiver 260 and, as such, the 50 and 53 kHz modulation may be used to control detectable levels of energy contained at those wavelengths. This control may be leveraged by embodiments of the present invention to maintain a relationship between $\lambda_{ABS}$ and $\lambda_{REF}$ at transmitter 210 and to detect changes in that relationship at receiver 260.

As illustrated in FIG. 2, electrical signal 213 may be generated by controller 218 to define and maintain the relationship between components 242, 244 in transmitted beam 240'. Additionally, generator 212 may provide one or more electrical signals 215 to controller 218 that is indicative of the spectral content of transmitted beam 240'. From such indication provided in signal 215, controller 218 may determine whether the prescribed relationship between components 242, 244 is properly maintained and may make suitable adjustments to electrical signal 213 accordingly.

Exemplary receiver 260 includes a collector 250 through which received beam 240" is accepted and provided to a detector 262. Collector 250 may include focusing elements by which beam 240" is focused onto an active area of detector 262, in response to which one or more electrical signals 263 may be generated. Electrical signal 263 may represent the spectral content of the received beam 240", i.e., the spectral content of beam 240 as transformed by the medium through which it has travelled. Electrical signal 263 may be provided to an analyzer 264, which may perform suitable spectral analyses on the received beam 240" to determine whether a deviation in the spectral content thereof is carried in the relationship between spectral components 242, 244 of the transmitted beam 240'. If so, as discussed above, the deviation may be reported as due to absorption of one or more of those spectral components by the medium.

Transmitter 210 and receiver 260 may be located along a line-of-sight path so that beam 240 can pass unidirectionally through the medium under scrutiny. That is, transmitter 210 and receiver 260 may be positioned in space such that scattered radiation from beam 240 in other than the forward direction from transmitter 210 is isolated from detector 262. Thus, absorption measurements by RAS 200 are free from noise contamination caused by backscattering, as is the case with conventional atmospheric absorption spectrometers.

Figure 3A:
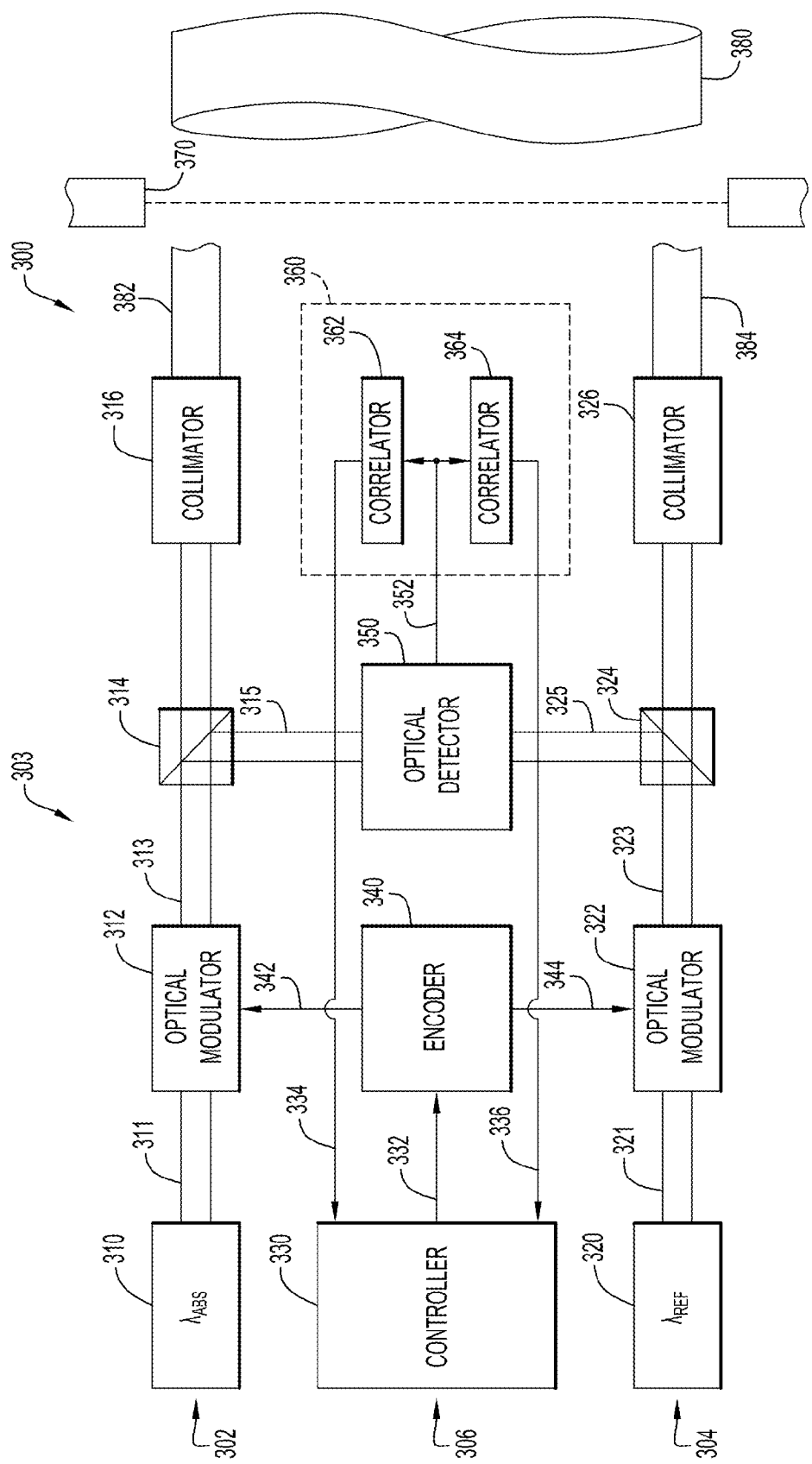
FIG. 3A is a schematic block diagram of an exemplary optical RAS transmitter embodying the present general inventive concept.
Figure 3B:
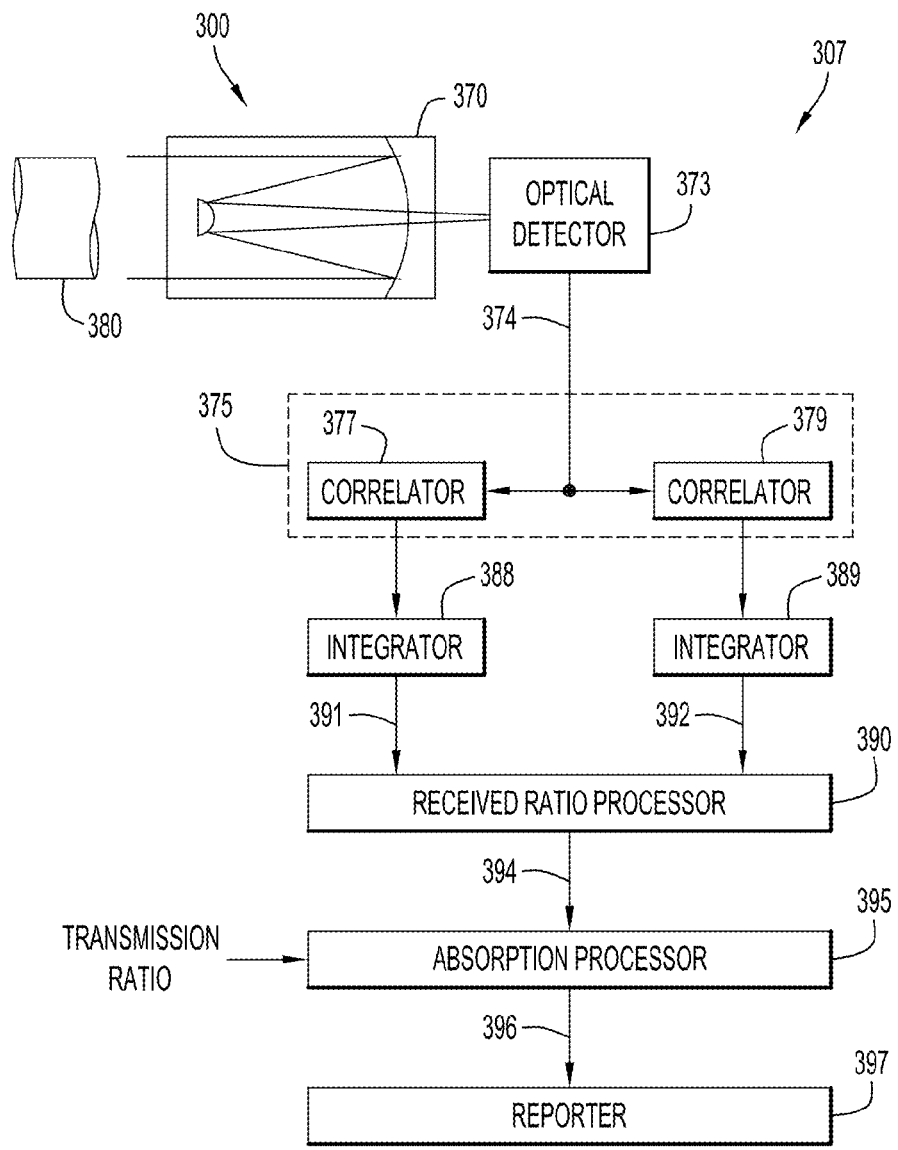
FIG. 3B is a schematic block diagram of an exemplary optical RAS receiver embodying the present general inventive concept.

FIG. 3A illustrates an exemplary transmitter 303 and FIG. 3B illustrates an exemplary receiver 307 of an optical RAS 300. Referring first to FIG. 3A, exemplary transmitter 303 comprises two optical channels: an absorption wavelength channel 302 and a reference wavelength channel 304. Optical channels 302, 304 incorporate respective optical radiation sources 310, 320, optical modulators 312, 322, beamsplitters 314, 324 and collimators 316, 326. The output of absorption channel 302 is a set of spectral components 382 and the output of reference channel 304 is a set of spectral components 384, both of which may be transmitted through a common aperture 370 in beam 380. The ordinarily skilled artisan will recognize and appreciate that aperture 370 may be other than a physical optical stop and it is to be understood that the explicit illustration of aperture 370 is to define an optical boundary of transmitter 303 for purposes of description and not limitation.

Radiation sources 310, 320 may be implemented by respective lasers emitting coherent light at wavelengths $\lambda_{ABS}$ and $\lambda_{REF}$, referred to herein as laser light 311 and laser light 321, respectively. Laser light 311, 321 may be modulated by optical modulators 312, 322 in accordance with selected codes. Optical modulators 312, 322 may be electro-optical devices independently operated at modulation frequencies suitable to apply the respective codes on laser light 311, 321. The modulated laser light 313, 323 may be sampled through the use of beamsplitters 314, 324, as will be described below, and provided to collimators 316, 326. Collimators 316, 326 may be implemented by suitable beam expanders through which the modulated light 313, 323 emerges from aperture 370 as a beam 380. It is to be understood that while, in certain embodiments, components 382, 384 may emerge from transmitter 303 in separate beams, such separated beams will be referred to herein as if such were contained in a single beam 380 for purposes of description and not limitation. It is to be understood further that, while separate collimators 316, 326 are illustrated in FIG. 3A, modulated light 313, 323 may be expanded through a single common collimator, as will be recognized by those skilled in the optical arts.

Exemplary transmitter 303 includes a control channel 306, by which the spectral content of optical channels 302, 304 is established and controlled. Control channel 306 may be implemented through suitable hardware, firmware and/or programmable processing hardware executing software, and may be constructed through analog and/or digital hardware. The ordinarily skilled artisan will readily recognize numerous control schemes by which control channel 306 can be embodied upon review of this disclosure. The scope of the present invention is intended to embrace all such embodiments of control channel 306.

Exemplary control channel 306 includes an encoder 340 to generate modulation codes in accordance with an electrical signal 332 provided thereto. RAS 300 is not limited to particular modulation codes; the codes can be chosen on an application basis in consideration of, for example, modulation and detection capabilities of the system components of RAS 300. Encoder 340 may generate electrical signals 342, 344 by which modulators 312, 322 are independently operated to apply the modulation codes on each optical channel 302, 304. Encoder 340 may generate, for example, amplitude modulation codes that are fixed in frequency. Control signal 332 may indicate to encoder 340 amplitude levels of respective codes applied to channels 302, 304 so that the relationship between spectral components 382, 384 is maintained. In certain embodiments, the relationship is a predetermined ratio between the transmitted optical energy in components 382 and that of components 384. When so embodied, exemplary encoder 340 modifies the amplitude of one or both codes in each optical channel 302, 304 so as to maintain the transmitted energy ratio. Electrical signals 342, 344 may be provided to modulators 312, 322, whereby modulated laser light 313, 323 is produced in each channel 302, 304.

Modulated light 313, 323 may be sampled, such as through beamsplitters 314, 324 and optical detector 350 for purposes of monitoring and control of the relationship between spectral components 382, 384. Optical detector 350 may be a monolithic optical device having a single active area sufficient in dimension to receive sampled beams 315, 325. In certain embodiments, focusing optics (not illustrated) may be inserted into the path between sampled beams 315, 325 and the active area of detector 350. Optical detector 350 should have sufficient dynamic range so as to respond to changes in the spectral range encompassing $\lambda_{ABS}$ and $\lambda_{REF}$ as modulation in each optical channel 302, 304 varies.

Detector 350 may generate an electrical signal 352 representative of changing spectral conditions in beam 380, which may be provided to a discriminator 360. Discriminator may, in turn, generate electrical signals 334, 336 indicative of the changing spectral conditions in each channel 302, 304, which may be provided to controller 330. Exemplary discriminator 362 includes correlators 362, 364, each configured in accordance with the modulation code of a corresponding optical channel 302, 304. Such correlators 362, 364 may be implemented through matched filters tuned to the modulation code in the corresponding optical channel 302, 304. When so embodied, the output of each correlator 362, 364 is a time-varying electrical signal 334, 336 indicative of the spectral energy transmitted in components 382, 384, which is proportional to the energy transmitted at wavelengths $\lambda_{ABS}$ and $\lambda_{REF}$, respectively.

Exemplary controller 330 is provided with signals 334, 336, whereby the relationship between transmitted energy in each channel 302, 304 is monitored and controlled. For example, if the prescribed relationship is $P(\lambda_{ABS})=r_0 \cdot P(\lambda_{REF})$, where P(X) is the power measured at detector 350 for channel X and extracted by discriminator 360, controller 330 may evaluate $P(\lambda_{ABS})/P(\lambda_{REF})$ from signals 334, 336 to determine a deviation $\Delta r$ of the evaluated ratio from the prescribed ratio $r_0$, e.g., $\Delta r=(r-r_0)$, where r is the ratio computed from signals 334, 336. A non-zero deviation $\Delta r$ may be reflected in control signal 332, responsive to which encoder 340 makes suitable adjustments to signals 342, 344 to increase and/or decrease $P(\lambda_{ABS})$ and/or $P(\lambda_{REF})$ in one or both of modulated light beams 313, 323.

FIG. 3B illustrates an exemplary receiver 307 for RAS 300. Receiver 307 may include receiving optics, such as telescope 370, by which beam 380, as transmitted by transmitter 303 and transformed by the medium under study, is accepted and focused onto detector 373. Detector 373 may be of construction similar, if not identical, to that of detector 350, although the present invention is not so limited. Detector 373 may generate an electrical signal 374 indicative of the changing spectral conditions in the received beam 380. The detector signal 374 may be provided to a discriminator 375, which may be of construction similar, if not identical, to that of discriminator 360, i.e., through correlators 377, 379, although the present invention is not so limited. The outputs of discriminator 375, are proportional to the spectral energy of each spectral component $\lambda_{ABS}$ and $\lambda_{REF}$ and may be provided to respective integrators 388, 389 to increase the signal-to-noise ratio in signals 391, 392. Integration by integrators 388, 389 may be through suitable summation techniques over time periods between seconds to tens of hours, depending on such factors as distance D between transmitter 303 and receiver 307 and composition of the medium. Signals 391, 392 may be provided to a received ratio processor 390, whereby the relationship $r_{eval}=P(\lambda_{ABS})/P(\lambda_{REF})$ is evaluated in a manner similar, if not identical, to the evaluation preformed by controller 330, although the present invention is not so limited. The received ratio processor 390 may generate an electrical signal 396 indicative of the evaluated ratio $r_{eval}$ which may be provided to absorption processor 397.

Exemplary absorption processor 395 determines absorption in the medium at $\lambda_{ABS}$ from an evaluation of $r_{eval}/r_0$. As discussed, RAS 300 is embodied to precisely govern the spectral content of beam 380 so that $\lambda_{ABS}$ lies in the absorption band of interest, $\lambda_{REF}$ is outside the absorption band of interest and the transmitted ratio $P(\lambda_{ABS})/P(\lambda_{REF})$ is maintained at $r_0$. Accordingly, absent any absorption at $\lambda_{ABS}$ by the medium, $r_{eval}/r_0$ is substantially unity. Deviations from unity in the evaluation of $r_{eval}/r_0$ can be attributed, with a reasonable degree of confidence, to absorption of the medium at $\lambda_{ABS}$. Absorption processor 395 may apply correction measures on $r_{eval}/r_0$ to account for, among other things, length of the transmission path, the direction of beam 380 through the medium, beam dispersion, the number of receivers and the manner in which the transmitted radiation is accepted thereby, e.g., simultaneous reception, temporally sequential, etc. An indication of compensated $r_{eval}/r_0$ may be conveyed in a signal 396 to a reporter 397, which may format results of the analysis by absorption processor 460 in a manner perceivable by a human user.

It is to be understood that the separation of functionality of components illustrated in FIGS. 3A-3B is solely for purposes of description and not limitation. Numerous alternative system configurations may implement a RAS 300 without departing from the spirit and intended scope thereof.

Figure 4:
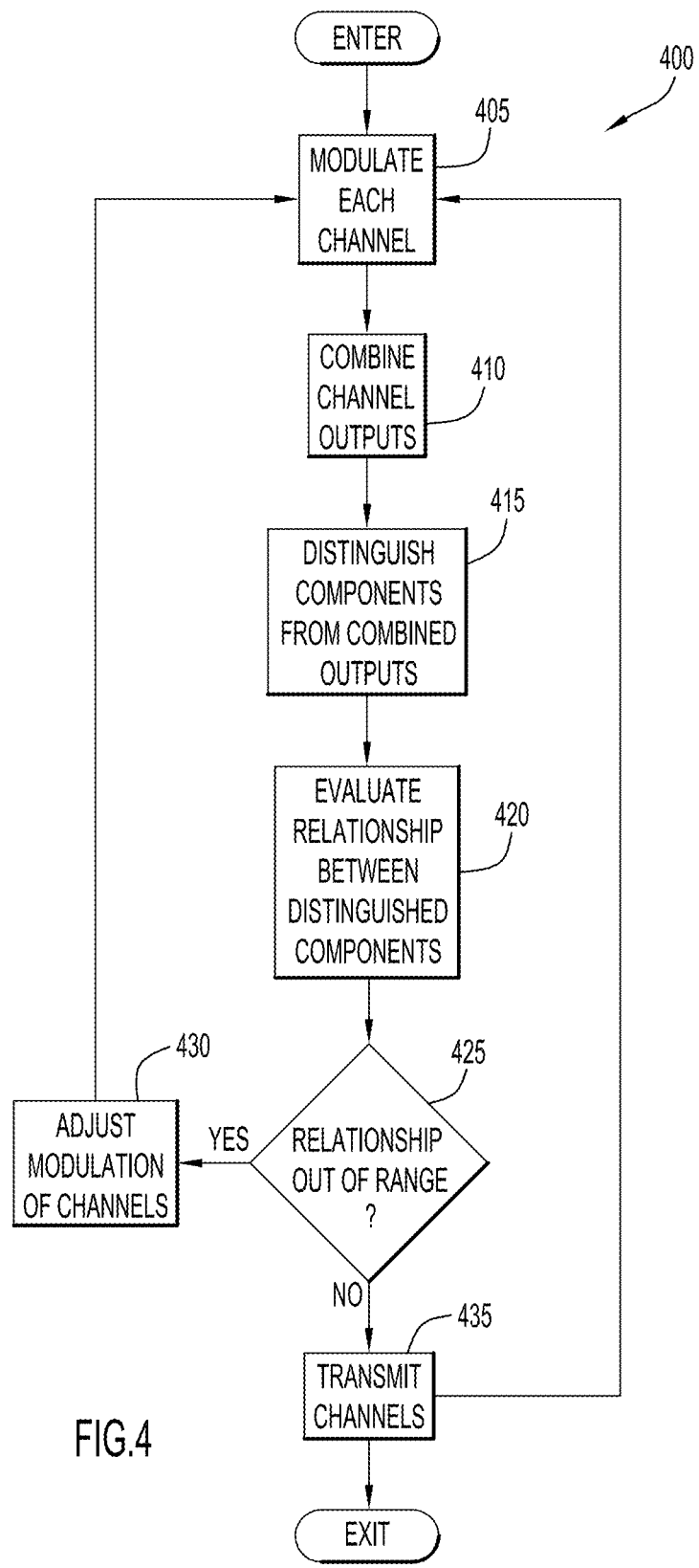
FIG. 4 is a flow diagram of a transmission process embodying the present general inventive concept.

FIG. 4 illustrates an exemplary transmission process 400 by which a RAS may transmit radiation for analysis by a receiver. In operation 405, radiation in respective channels, such as those illustrated by channels 302, 304 of RAS 300, is modulated in accordance with codes assigned to each channel. The modulated radiation is combined in operation 410, such as by provision to a common detector 350, and, in operation 415, the combined radiation is distinguished into separate components, e.g., the spectral component in the absorption band and the spectral component in the off-line band, such as by discriminator 360. In operations 420 and 425, the distinguished spectral components are evaluated to determine whether a relationship therebetween defined by the codes is within a predetermined range. If not, the modulation is adjusted in operation 430, such as by increasing or decreasing modulation amplitude, to maintain the relationship. If the relationship is within tolerance, as determined in operation 425, the components are transmitted in a beam in operation 435.

Figure 5:
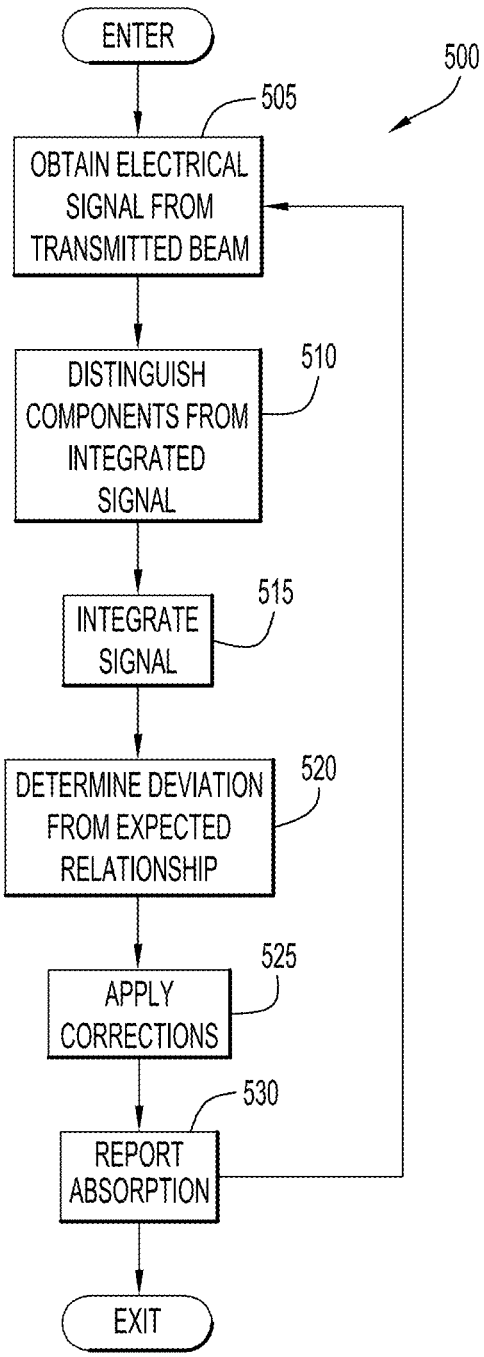
FIG. 5 is a flow diagram of an exemplary analysis process embodying the present general inventive concept.

FIG. 5 illustrates an exemplary analysis process 500 usable with transmission process 400. In operation 505, an electrical signal is obtained from the transmitted beam, such as by detector 420. In operation 510, the spectral components are distinguished, such as in a manner similar to that of operation 415 in process 400, and the signals are integrated over a selected time interval in operation 515, such as by integrator 430. In operation 520, the integrated spectral components are evaluated to determine whether a deviation exists in the relationship therebetween defined by the codes and the relationship between the received spectral components. In operation 525, such deviation is compensated for system and transmission path-dependent variability and the corrected deviation is reported as absorption by the medium in operation 530.

Figure 6:
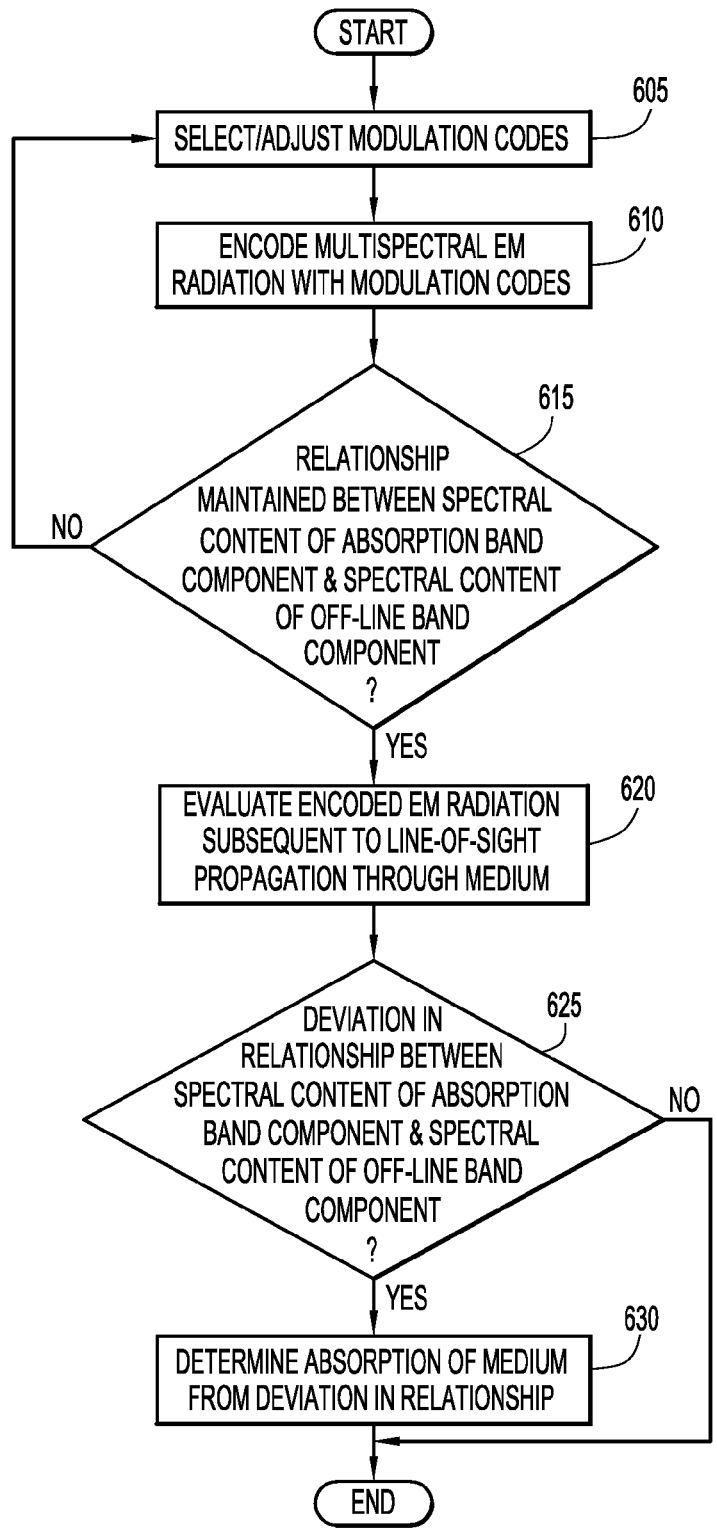
FIG. 6 is a flow diagram of a processor-executable process embodying the present general inventive concept.

FIG. 6 is a flow diagram of a processor-executable process 600 by which the present invention can be embodied. In operation 605, modulation codes are selected and, in operation 610, multispectral electromagnetic radiation is modulated with the selected modulation codes. In operation 615, it is determined whether a relationship is maintained between spectral content of an absorption band component of the multispectral electromagnetic radiation and spectral content of an off-line band component of the multispectral electromagnetic radiation. If the relationship is not maintained, process 600 may transition back to operation 605 by which the modulation codes are adjusted. If, however, the relationship is maintained as determined in operation 615, process 600 may transition to operation 620 by which the encoded electromagnetic radiation is evaluated subsequent to line-of-sight propagation through a medium. In operation 625, it is determined whether the evaluation reveals a deviation in the relationship determines between the spectral content of the absorption band component and the spectral content of the off-line band component subsequent to propagation through the medium. Absorption of the medium may be determined from the deviation in the relationship in operation 630.

The descriptions above are intended to illustrate possible implementations of the present inventive concept and are not restrictive. Many variations, modifications and alternatives will become apparent to the skilled artisan upon review of this disclosure. For example, components equivalent to those shown and described may be substituted therefore, elements and methods individually described may be combined, and elements described as discrete may be distributed across many components. The scope of the invention should therefore be determined not with reference to the description above, but with reference to the appended claims, along with their full range of equivalents.

What is claimed is:
1. An apparatus comprising:
a generator configured to generate multispectral electromagnetic radiation having at least one spectral component having a wavelength coinciding with an absorption band of a known substance and at least one spectral component having a wavelength coinciding with an off-line band that is removed from the absorption band wavelength;

a transmitter configured to:
  modulate the generated spectral components with respective modulation codes that define a predetermined relationship between spectral content of the modulated spectral component having the absorption band wavelength and the spectral content of the modulated spectral component having the off-line band wavelength;
  modify the modulation codes in response to determining that the relationship between the spectral content of the modulated spectral component having the absorption band wavelength and the spectral content of the modulated spectral component having the off-line band wavelength is other than the predetermined relationship; and
  transmit the modulated radiation through a medium; and
at least one receiver spatially isolated from the transmitter and arbitrarily locatable with respect thereto, the receiver configured to:
  accept the transmitted radiation through line-of-sight propagation through the medium;
  measure the relationship between the absorption band spectral content and the off-line band spectral content of the received radiation; and
  determine absorption at the wavelength coinciding with the absorption band from a deviation of the measured relationship between the absorption band spectral content and the off-line band spectral content from the predetermined relationship.

2. The apparatus of claim 1, wherein the transmitter includes:
  a radiation channel for each spectral component in the absorption band and for each spectral component in the off-line band, each radiation channel modulating the corresponding spectral component such that the relationship therebetween is maintained.

3. The apparatus of claim 2, wherein the transmitter includes:
  a modulator in each radiation channel configured to modulate the corresponding spectral component by the respective modulation codes in accordance with respective control signals provided thereto;
  a detector configured to generate an electrical signal from the modulated radiation incident thereon from the radiation channel of at least one spectral component in the absorption band and the radiation channel of at least one spectral component in the off-line band; and
  a controller configured to generate the control signals responsive to the detector signal so as to maintain the relationship between the absorption band spectral content and the off-line band spectral content.

4. The apparatus of claim 3, wherein the controller includes an encoder to generate modulation codes for respective radiation channels and to provide an indication of the codes in the control signals, the encoder modifying a parameter of the codes so as to maintain the relationship between the absorption band spectral content and the off-line band spectral content at the predetermined relationship.

5. The apparatus of claim 4, wherein the codes identify the respective radiation channels of the transmitter at the receiver.

6. The apparatus of claim 4, wherein the codes are amplitude modulation codes and the parameter thereof is signal amplitude.

7. The apparatus of claim 4, wherein the controller includes a discriminator to generate discriminator signals responsive to the signal from the detector such that the discriminator signals represent transmitted energy in the modulated spectral component having the absorption band wavelength and in the modulated spectral component having the off-line band wavelength.

8. The apparatus of claim 7, wherein discriminator includes a correlator for each radiation channel, the correlator being tuned to the code assigned to the corresponding radiation channel to provide a corresponding one of the discriminator signals responsive to the detector signal.

9. The apparatus of claim 3, wherein the receiver includes:
  a detector configured to generate a receiver signal from the received radiation incident thereon; and
  an analyzer configured to measure the relationship between the absorption band spectral content and the off-line spectral content from the receiver signal and to compute the absorption at the wavelength coinciding with the absorption band from the deviation of the measured relationship between the absorption band spectral content and the off-line band spectral content from the predetermined relationship.

10. The apparatus of claim 9, wherein the analyzer includes a discriminator to generate discriminator signals responsive to the receiver signal from the detector, each of the discriminator signals representing energy in a corresponding spectral component of the received radiation including the absorption band spectral component and the off-line band spectral component.

11. The apparatus of claim 10, wherein discriminator includes a correlator for each spectral component to be analyzed, the correlator being tuned to the code assigned to the corresponding spectral component to provide a corresponding one of the discriminator signals responsive to the receiver signal.

12. The apparatus of claim 1, wherein the transmitter and receiver are independently locatable in a substantially boundless medium.

13. The apparatus of claim 12, wherein the at least one receiver comprises a plurality of receivers substantially identical to the at least one receiver.

14. The apparatus of claim 13, wherein the transmitter includes a beamformer by which the transmitted radiation is distributed to be simultaneously accepted by the receivers.

15. The apparatus of claim 13, wherein the transmitter includes a movable platform by which the transmitter traverses a trajectory through which the radiation transmitted therefrom is accepted by the receivers in a sequence defined by the trajectory.

16. A method comprising:
  generating by a transmitter multispectral electromagnetic radiation including at least one spectral component having a wavelength coinciding with an absorption band of a known substance and at least one spectral component having a wavelength coinciding with an off-line band that is removed from the absorption band wavelength;
  modulating the generated spectral components with respective modulation codes that define a predetermined relationship between spectral content of the modulated spectral component having the absorption band wavelength and the spectral content of the modulated spectral component having the off-line band wavelength;
  modifying the modulation codes in response to determining that the relationship between the spectral content of the modulated spectral component having the absorption band wavelength and the spectral content of the modulated spectral component having the off-line band wavelength is other than the predetermined relationship;
  transmitting the modulated radiation through a medium;

accepting at a receiver the transmitted radiation through line-of-sight propagation through the medium;

measuring the absorption band spectral content and the off-line band spectral content; and determining absorption at the wavelength coinciding with the absorption band from a deviation of the relationship between the measured absorption band spectral content and the measured off-line spectral content from the predetermined relationship.

17. The method of claim 16, wherein modulating the spectral components includes:

encoding the spectral component having the absorption band wavelength and the spectral component having the off-line band wavelength with respective modulation codes; and modifying a parameter of the codes so as to maintain the predetermined relationship between the spectral content of the modulated spectral component having the absorption band wavelength and the spectral content of the modulated spectral component having the off-line band wavelength.

18. The method of claim 17, wherein:

measuring the absorption band spectral content and the off-line band spectral content includes correlating a representation of the received radiation with the codes to produce a representation of the received spectral component having the absorption band wavelength and a representation of the spectral component having the off-line band wavelength; and determining the absorption includes determining a difference between the predetermined relationship and the relationship between the spectral component representations produced by the correlating and establishing the difference as the deviation.

19. The method of claim 18 further comprising:

establishing as the predetermined relationship a predetermined proportionality between energy in the modulated spectral component having the absorption band wavelength and the energy in the modulated spectral component having the off-line band wavelength.

20. The method of claim 19, wherein the determining of the absorption includes:

attributing to the absorption by the known substance in the medium the difference between the proportionality of the energy in the received spectral component having the absorption band wavelength to the energy in the received spectral component having the off-line band wavelength and the predetermined proportionality.

21. A non-transitory computer readable medium encoded with software comprising processor-executable instructions that, when executed by a processor, cause the processor to perform functions of:

encoding components of multispectral electromagnetic radiation with a plurality of modulation codes to define a predetermined relationship between spectral content of at least one of the modulated spectral components having a wavelength coinciding with an absorption band of a known substance and the spectral content of at least one spectral component having a wavelength coinciding with an off-line band that is removed from the absorption band wavelength;

modifying the modulation codes in response to determining that the relationship between the spectral content of the modulated spectral component having the absorption band wavelength and the spectral content of the modulated spectral component having the off-line band wavelength is other than the predetermined relationship;

measuring the absorption band spectral content and the off-line band spectral content of the encoded radiation subsequent to line-of-sight propagation thereof through a medium; and determining absorption at the wavelength coinciding with the absorption band from a deviation of the relationship between the measured absorption band spectral content and the measured off-line spectral content from the predetermined relationship.

* * * * *